United States Patent [19]
Kinsinger et al.

[11] Patent Number: 5,623,921
[45] Date of Patent: Apr. 29, 1997

[54] LARYNGEAL MASK AIRWAY AND METHOD FOR ITS USE

[76] Inventors: J. William Kinsinger, 12000 Windflower Pl., Oklahoma City, Okla. 73120; William A. Beck, 500 Napa Valley, Apt. 536, Little Rock, Ark. 72211

[21] Appl. No.: 633,845

[22] Filed: Apr. 10, 1996

[51] Int. Cl.$^6$ .................................................. A61M 16/00
[52] U.S. Cl. ................................ 128/200.26; 128/207.15
[58] Field of Search .................... 128/200.26, 207.14, 128/207.15, 912, DIG. 26

[56] References Cited

U.S. PATENT DOCUMENTS

| | | | |
|---|---|---|---|
| 4,412,832 | 11/1983 | Kling et al. | 604/164 |
| 4,449,526 | 5/1984 | Elam | 128/206.21 |
| 4,995,388 | 2/1991 | Brain | 128/207.15 |
| 5,167,634 | 12/1992 | Corrigan, Jr. et al. | 604/160 |
| 5,241,956 | 9/1993 | Brain | 128/207.15 |
| 5,282,464 | 2/1994 | Brain | 128/207.15 |
| 5,297,547 | 3/1994 | Brain | 128/207.15 |
| 5,303,697 | 4/1994 | Brain | 128/200.26 |

OTHER PUBLICATIONS

Pennant, J. H. et al., "The Laryngeal Mask Airway–Its Uses In Anesthesiology", *Anesthesiology*, v. 79, No. 1, Jul. 1993, pp. 144–163.

Pennant, J. H. et al., "Intubation Through the Laryngeal Mask Airway", *Anesthesiology*, v. 83, No. 4, Oct. 1995, p. 891.

Brimacombe, J. et al., "Modified Intravent LMA", *Anaesthesia And Intensive Care*, vol. 19, No. 4, Nov., 1991.

Hornbein, T. F. et al., "Another Way Through A Laryngeal Mask Airway", *Anesthesiology*, v. 83, No. 4, Oct. 1995, p. 880.

"Difficult Airway Algorithm", American Society Of Anesthesiologists.

"LMA–Advancing Airway Management", Gensia, Inc., San Diego, Ca.

*Primary Examiner*—Aaron J. Lewis
*Attorney, Agent, or Firm*—William R. Sharp

[57] ABSTRACT

A laryngeal mask airway (LMA) is provided which can be easily and effectively used to intubate a patient with an endotracheal tube (ETT). The LMA of the invention is of the type having an inflatable mask and an airway tube connected to the mask. The airway tube comprises a first tube section having a distal end connected to the mask, and a second tube section having a distal end removably connected to the proximal end of the first tube section. The second tube section has longitudinally extending separation lines which allow it to be split apart. This feature enables complete removal of the LMA and successful incubation with the cuff of the ETT below the vocal cords of the patient.

11 Claims, 4 Drawing Sheets

LARYNGEAL MASK AIRWAY AND METHOD FOR ITS USE

This invention relates to a laryngeal mask airway and a method for its use in intubation with an endotracheal tube. As used hereafter, "ETT" indicates an endotracheal tube, and "LMA" indicates a laryngeal mask airway.

The ETT is the most typical and effective device for ventilating the lungs of a patient, particularly an unconscious patient under general anesthesia. The ETT comprises a flexible tube which has an inflatable cuff near its distal end. The ETT is inserted into the trachea, a procedure called "intubation", and the cuff inflated below the vocal cords to seal the trachea and provide protection against the passage of regurgitated stomach contents into the trachea. It is important that the cuff is below the vocal cords to provide a proper seal and avoid damage to the vocal cords. In some patients, conventional intubation is very difficult or impossible.

The LMA is a more recently developed alternative ventilation device. The LMA comprises an airway tube and an inflatable mask at the distal end of the airway tube. The mask can be easily inserted into the pharynx of the patient and then inflated to seal against the laryngeal inlet. The LMA has the disadvantage of not adequately preventing the passage of regurgitated stomach contents into the trachea. The LMA also does not guarantee the ability to provide positive pressure ventilation.

A recently developed technique involves using the LMA as a guide for insertion of the ETT. In 1993, the American Society of Anesthesiologists added this technique to its Difficult Airway Algorithm. According to this technique, the LMA is placed in its normal position adjacent to the laryngeal inlet, and the ETT is then inserted into the airway tube of the LMA, through the mask, and into the trachea. In some patients, especially men, the standard 6.0 ETT, having an inside diameter of 6.0 mm and a length of 28.5 cm, will not extend into the trachea a sufficient distance to position the ETT cuff below the vocal cords. This problem, as well as a number of proposed solutions, is discussed in an article entitled "Intubation through the Laryngeal Mask Airway" by John H. Pennant et al, *Anesthesiology*, V. 84, No. 4, October 1995. Such solutions include: use of a 5.0 mm microlaryngeal tube, which is longer than the standard 6.0 ETT; use of a shortened version of the LMA (the ST-LMA); and cutting off about 2 cm of the LMA airway tube. Yet another proposed solution is discussed in an article entitled "Modified Intravent LMA" by J. Brimacombe et al., *Anaesthesia and Intensive Care*, Vol. 19, No. 4, November 1991. Brimacombe's solution involves drastic modifications of an LMA which include a slit from the proximal end of the LMA to its distal aperture, and removal of the mask aperture cross-bars.

Each of the proposed solutions suffer from at least one of the following problems, wherein the above-mentioned proposed solutions having such problems are indicated in parentheses: (1) does not employ standard 6.0 ETT (5.0 microlaryngeal tube); (2) does not maintain the structural integrity of the LMA mask (solution of Brimacombe); and (3) does not allow removal of the LMA from the patient while leaving the ETT in place, because an insufficient length of the ETT is exposed (cutting off 2 cm of LMA tube and shortened LMA). The ETT must be held in position while removing the LMA. Otherwise, the ETT will tend to be removed from its desired position when the LMA is removed. A sufficient length of the ETT must be exposed in order to grasp the ETT while simultaneously removing the LMA.

With respect to problem (1), the standard 6.0 ETT as compared to the 5.0 microlaryngeal tube has a lower resistance to gas flow and typically is more efficacious in providing adequate ventilation and oxygenation. Problem (2) does not allow reuse of the LMA, and does not allow ventilation with the LMA. With respect to problem (3), leaving the LMA in place with the ETT can make certain types of surgeries, such as facial, oral, or throat surgery, difficult or impossible. It is also frequently desirable to stabilize the ETT with tape or some other means at the mouth of the patient, and/or to insert a nasal or oral gastric tube into the patient. Neither of these procedures can be carried out when the LMA is left in the patient. If long term intubation is necessary (i.e. subsequent to a surgical procedure), oral hygiene and clearing of secretions is difficult with the LMA in place. Prolonged placement can also lead to injury or edema in the oropharyngeal cavity.

SUMMARY OF THE INVENTION

It is, therefore, an object of the invention to provide an LMA which can be used to intubate a patient with an ETT so as to guarantee placement of the cuff below the vocal cords.

It is also an object of the invention that the LMA allows use of a standard 6.0 ETT, maintains the structural integrity of the mask, and allows easy removal of the LMA from the patient while leaving the ETT in the trachea.

The above objects are realized by an LMA of the type having an inflatable mask for sealing around the laryngeal inlet of a patient, and also having an airway tube connected to the mask and being adapted to deliver air therethrough to the mask and the laryngeal inlet, wherein the airway tube comprises: a first tube section having a first proximal end and a first distal end, the first distal end being connected to the mask; and a second tube section having a second proximal end and a second distal end, the second distal end being removably connected to the first proximal end, and wherein the second tube section has a pair of radially opposite separation lines longitudinally extending from the second proximal end to the second distal end to thereby allow the second tube section to be split apart along the separation lines.

According to another aspect of the invention, there is provided a method of intubating a patient with an ETT by using an LMA, wherein the ETT is of the type which comprises a tube having a proximal end, a distal end, and an inflatable cuff adjacent to the distal end, and wherein the LMA is of the type described above, the method comprising: (a) providing an airway tube for the LMA as described above; (b) inserting the LMA into the patient so that the mask is positioned immediately adjacent to the laryngeal inlet; (c) after step (b), inserting the ETT through the airway tube and through the mask so as to extend into the trachea of the patient; (d) after step (c), peeling away the second tube section by splitting it apart along the separation lines; and (e) during or after step (d), further inserting the ETT into the trachea to position its cuff below the vocal cords of the patient.

DETAILED DESCRIPTION OF THE INVENTION

A preferred embodiment of the invention will now be described with reference to the FIGURES.

Figure 1:
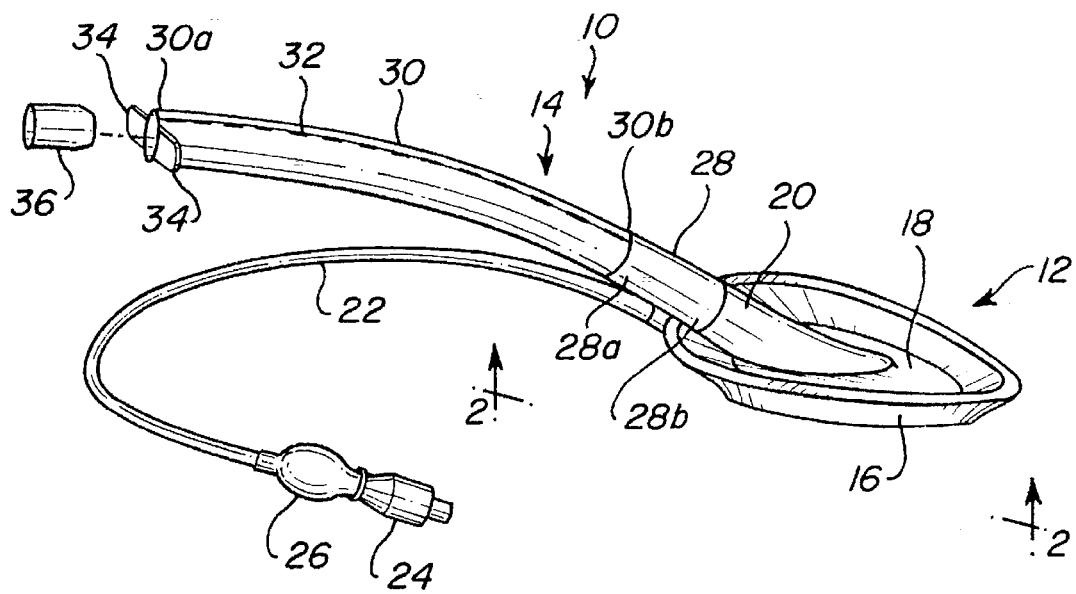
FIG. 1 is a perspective view of an LMA in accordance with the invention.

Referring to FIG. 1, the illustrated LMA 10 is of the type having an inflatable mask 12 and an airway tube 14 connected to mask 12 and being adapted to deliver air therethrough to mask 12. Mask 12 is shown as being in a deflated state, and is conventional in having an inflatable ring 16, a web 18, and a tubular inlet member 20 having one end integral with web 18 and the other end permanently connected to airway tube 14 in the manner described below. Mask 12 is preferably comprised of flexible silicone rubber. An inflation tube 22, also preferably silicone rubber, is connected at one end to ring 16 so as to communicate with its interior. At the other end of inflation tube 22 is a check valve 24 having a pilot bulb 26 associated therewith. Pilot bulb 26 has approximately the same capacity as ring 16, and serves as an inflation indicator.

Airway tube 14 comprises a tube section 28 and a tube section 30. Tube section 28 is preferably shorter in length than tube section 30, and is most preferably about one inch long where LMA 10 is a size 3 or 4 LMA. Tube section 28 has a proximal end 28a and a distal end 28b, and tube section 30 has a proximal end 30a and a distal end 30b. Distal end 28b is fixedly and permanently connected (i.e. by welding) to inlet member 20, and proximal end 28a is removably connected to distal end 30b in a manner described with reference to FIG. 3. Tube section 30 has a pair of radially opposite separation lines 32 longitudinally extending from proximal end 30a to distal end 30b. Only one separation line 32 is shown in FIG. 1. Separation lines 32 are preferably formed by scoring the wall of tube section 30. Since it is desired that LMA 10 be usable to ventilate the lungs of a patient, separation lines 32 are preferably impermeable to air. As will be further discussed with reference to FIG. 7, separation lines 32 allow tube section 30 to be split apart. To assist the user in splitting apart, or peeling away, tube section 30, a pair of radially opposite wings 34 are provided at proximal end 30a. Wings 34 radially and outwardly extend from proximal end 30a at respective positions circumferentially offset from separation lines 32.

The material employed for tube section 30 can be any nontoxic and sterilizable material that is peelable along separation lines 32. Such material should preferably have at least some flexiblity. Flexible polyvinyl chloride and silicone rubber are preferred with regard to flexibility, but semi-rigid materials such as polyethylene or tetrafluroethylene could also be used if tube section 30 Was suitably preshaped to approximate the necessary contour for placement in the patient. Wings 34 can be integral with and be the same material as tube section 30. Or, wings 34 can be comprised of a different material and be permanently connected to proximal end 30a. The material for tube section 28 can be the same as or different than the material employed for tube section 30. Silicone rubber is preferred.

Also shown in FIG. 1 is a connector 36 as removed from proximal end 30a. Connector 36, preferably comprised of a substantially rigid plastic, is adapted to be tightly and sealingly received in tube section 30 at proximal end 30a. A breathing circuit can be connected to LMA 10 by means of connector 36.

Figure 2:
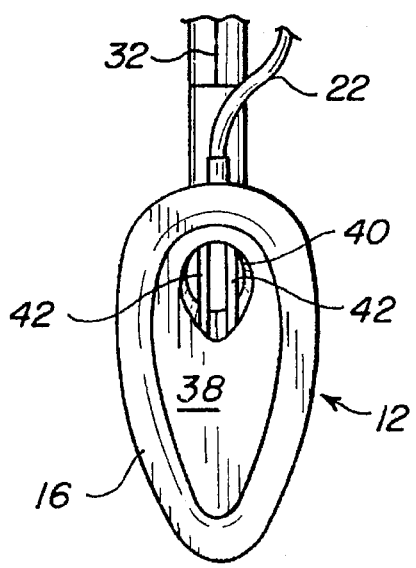
FIG. 2 is a view of the LMA of FIG. 1 as viewed along line 2—2 in FIG. 1.

Referring now to FIG. 2, this partial view of LMA 10 shows the other separation line 32 as well as other details of mask 12. Mask 12 further has an interior or lumen 38, an aperture 40 into which inlet member 20 opens, and crossbars 42 which extend across aperture 40.

Figure 3:
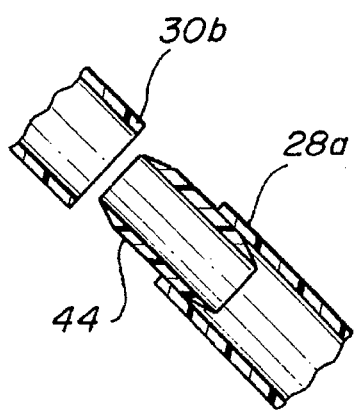
FIG. 3 is an enlarged, cross-sectional view of a portion of the LMA shown in FIGS. 1 and 2.

Referring now to FIG. 3, this enlarged and partial cross-sectional view shows the manner in which proximal end 28a and distal end 30b are removably connected. Connector 44, comprised of any suitably rigid plastic, preferably has tapered ends and an intermediate portion of substantially uniform diameter along the length thereof. One portion of connector 44 is received in, and preferably permanently secured within, proximal end 28a, and the other portion of connector 44 is sized to be tightly and removably received within distal end 30b. FIG. 3 shows distal end 30b as being disconnected from proximal end 28a. Connector 44 preferably has an inside diameter large enough to receive a 6.0 ETT therethrough.

The use of LMA 10 in intubating a patient with an ETT will now be described with reference to FIGS. 4–9. It should be understood that the anesthesiologist's and/or technician's hands are not shown for clarity of illustration. The hand(s) of at least one person manipulate(s) LMA 10 and the ETT as shown in FIGS. 4–9.

Figure 4:
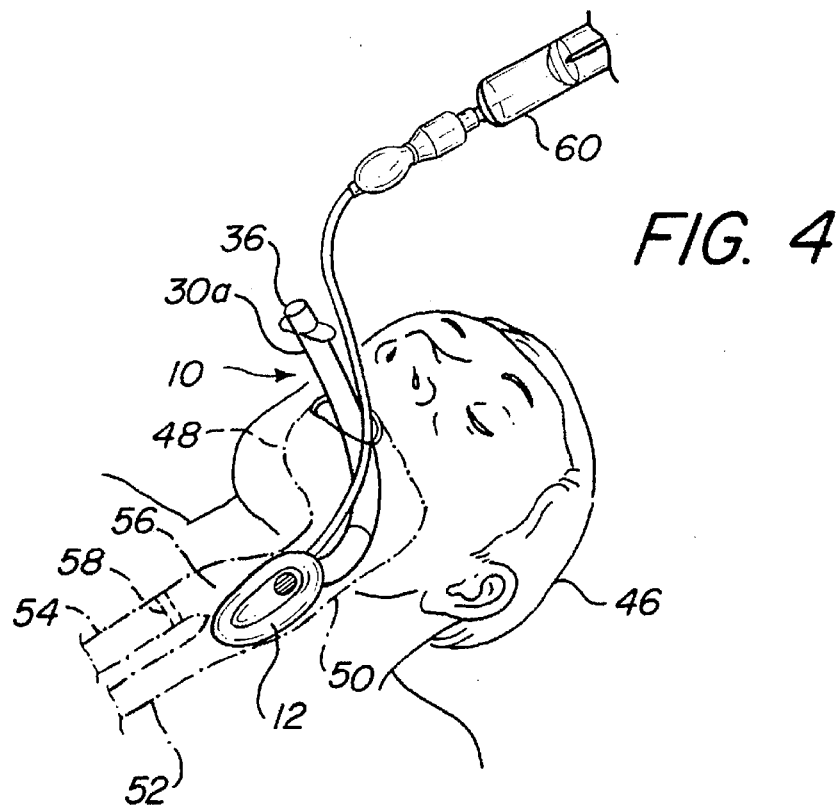
FIGS. 4–9 show the LMA of FIGS. 1–3 in use to intubate a patient with an ETT.

Referring now to FIG. 4, there is shown a patient 46 having an oral cavity 48, a throat 50, an esophagus 52, a trachea 54, a laryngeal inlet 56, and vocal cords 58. Mask 12 of LMA 10 is positioned immediately adjacent to laryngeal inlet 56 and is inflated with a syringe 60 or other suitable means to establish a seal around laryngeal inlet 56. Connector 36 is received within proximal end 30a to allow connection to a breathing circuit (not shown). It is desirable at this point to briefly ventilate the lungs of patient 46 with LMA 10 in order to oxygenate the patient and confirm the correct placement of the LMA.

Figure 5:
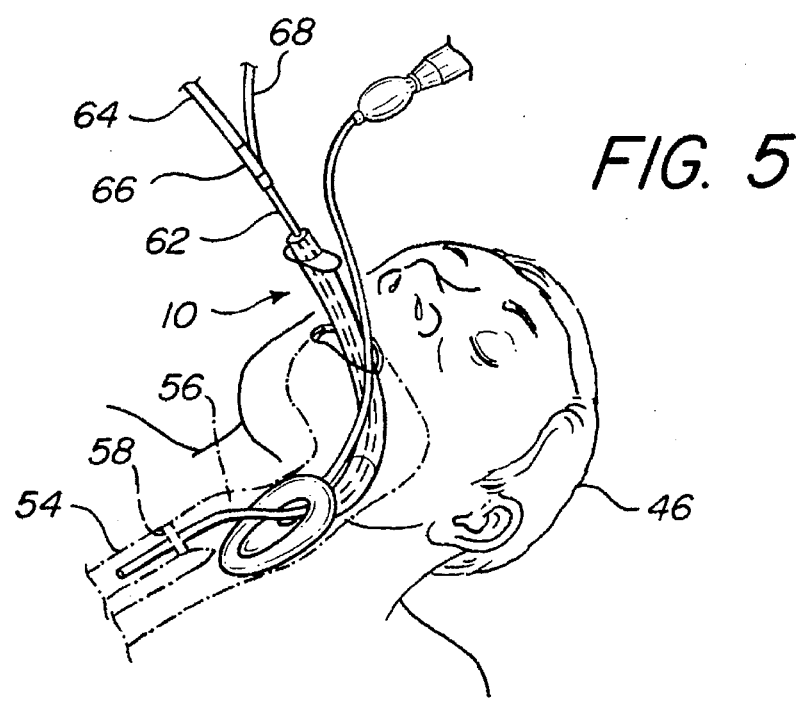

Referring now to FIG. 5, there is shown a fiberoptic tube 62 of a bronchoscope after having been preloaded with an ETT 64 (preferably a 6.0 ETT) and inserted through LMA 10 so as to extend into trachea 54. The distal end of fiberoptic tube 62 is positioned below vocal cords 58 as shown. Use of the bronchoscope and its fiberoptic tube 62 is desirable since the anesthesiologist can view the position of the fiberoptic tube's distal end, thereby easing the task of locating laryngeal inlet 56. ETT 64, having a deflated cuff 66 and inflation tube 68, is preloaded onto fiberoptic tube 62 since a handpiece (not shown) connected to the proximal end of fiberoptic tube 62 would not permit sliding of ETT 64 over the fiberoptic tube once it is inserted into patient 46.

Figure 6:
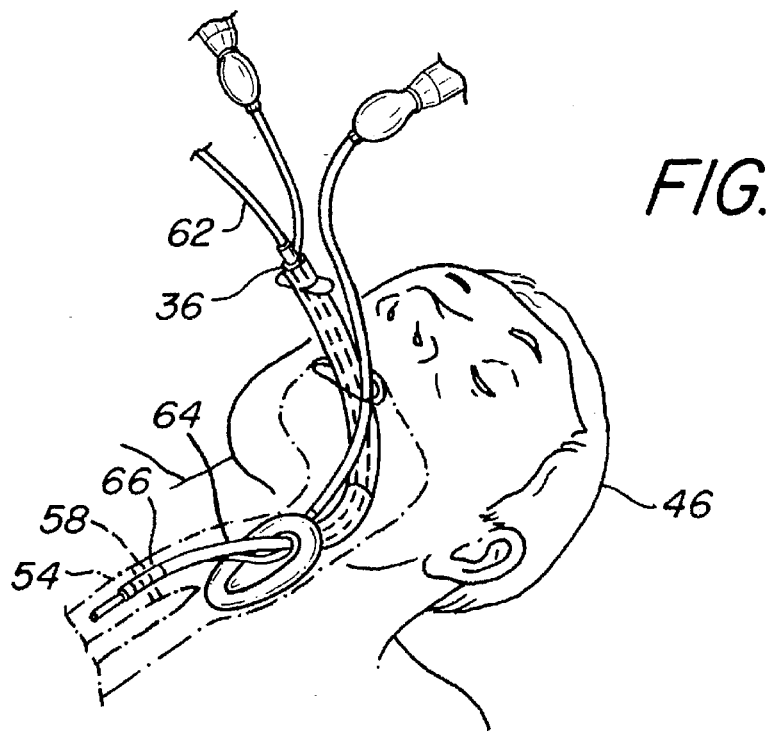

Referring now to FIG. 6, ETT 64 is shown after having been moved downward over fiberoptic tube 62 and into trachea 54. As shown, in this particular patient 46, cuff 66 is not positioned below vocal cords 58 as desired. Fiberoptic tube 62 can now be removed while holding the proximal end of ETT 64 to prevent unintended withdrawal of the ETT.

Figure 7:
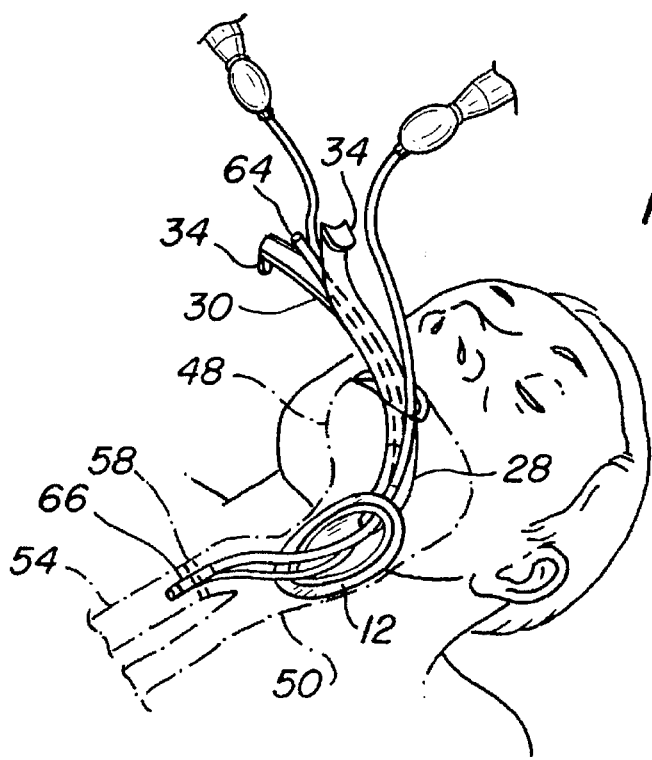

Referring now to FIG. 7, after removing fiberoptic tube 62 and also deflating ring 16, a first person grasps opposing wings 34 with each hand, and a second person holds ETT 64. The first person then pulls on each wing 34 to start peeling away tube section 30, thereby causing connector 36 (FIG. 6) to simply fall away if not previously removed. As tube section 30 is peeled away by the first person, mask 12 and tube section 28 are gradually withdrawn through throat 50 and oral cavity 48, while at the same time ETT 64 can be advanced further into trachea 54 by the second person. Once tube section 30 is completely peeled away, mask 12 and tube section 28 are moved upwardly by the first person to completely remove them from ETT 64, while the second person continues to hold ETT 64 to prevent its unintended withdrawal. Mask 12 and tube section 28 can be sterilized and reused with a new, peelable tube section.

Figure 8:
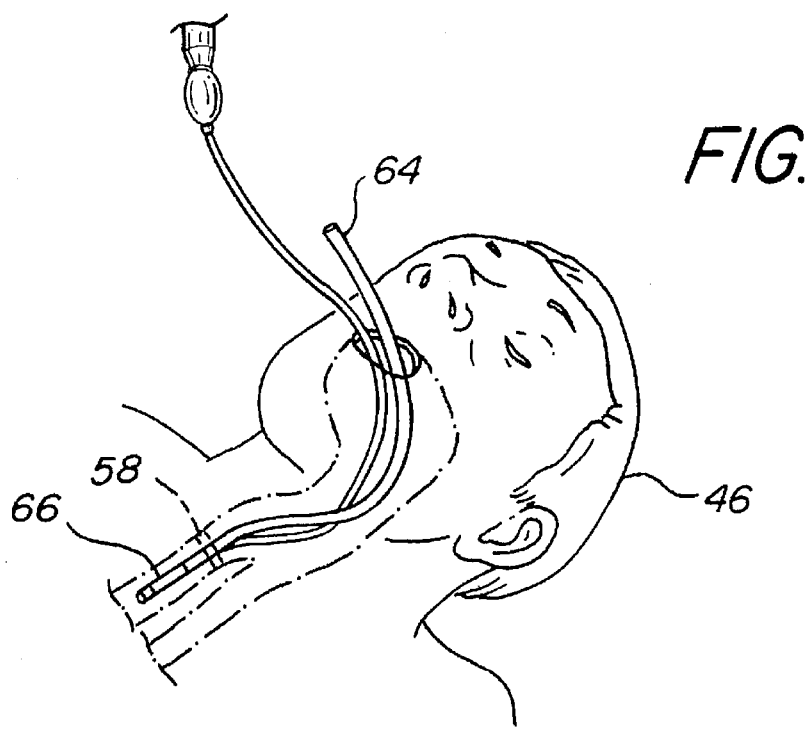
Figure 9:
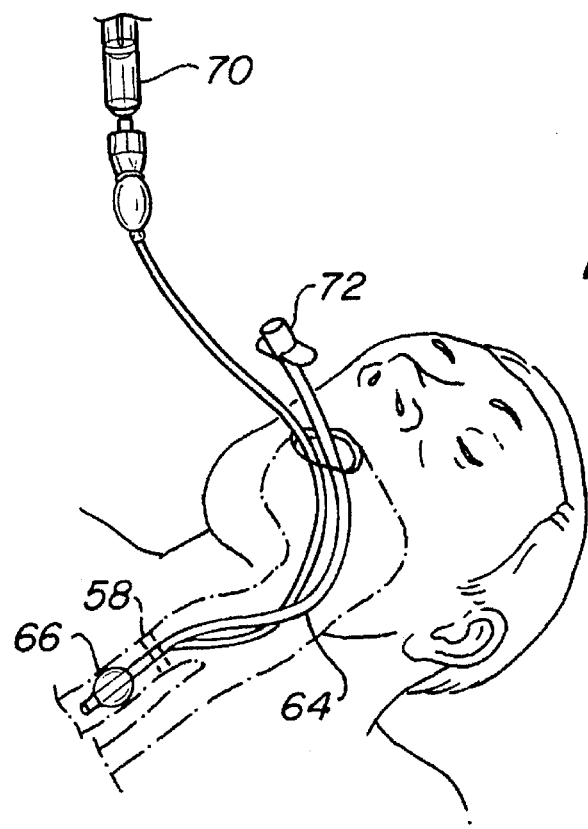

Referring now to FIG. 8, ETT 64 is shown after the LMA is completely removed therefrom and from patient 46. ETT 64 is shown after having been advanced to its desired position with cuff 66 below vocal cords 58. FIG. 9 shows ETT 64 in this desired position after having cuff 66 inflated with syringe 70 or other suitable means. FIG. 9 also shows a conventional breathing circuit connector 72 received within the proximal end of ETT 64. A breathing circuit can accordingly be connected to ETT 64 by means of connector 72 to start normal ventilation.

Therefore, the LMA of the invention successfully achieves intubation with an ETT, and also allows use of a standard 6.0 ETT, maintains the structural integrity of the mask for ventilation and reuse, and allows its easy removal while leaving the ETT in place.

Obviously, many modifications and variations of the present invention are possible in light of the above teachings. For example, rather than use a connector to removably connect proximal end 28a to distal end 30b, such ends could be adapted to removably mate with one another without requiring a connector. With regard to the method of using the inventive LMA, the LMA could be used in a "blind" intubation without using the bronchoscope. It is, therefore, to be understood the within the scope of the appended claims, the invention can be practiced otherwise than as specifically described.

That which is claimed is:

1. A laryngeal mask airway having an inflatable mask for sealing around a patient's laryngeal inlet, and also having an airway tube connected to the mask and being adapted to deliver air therethrough to the mask and a patient's laryngeal inlet, wherein the airway tube comprises:

a first tube section having a first proximal end and a first distal end, the first distal end being connected to the mask; and a second tube section having a second proximal end and a second distal end, the second distal end being removably connected to the first proximal end, and wherein the second tube section has a pair of radially opposite separation lines longitudinally extending from the second proximal end to the second distal end to thereby allow the second tube section to be split apart along the separation lines.

2. A laryngeal mask airway as recited in claim 1 wherein the separation lines are scored and are impermeable to air.

3. A laryngeal mask airway as recited in claim 2 wherein the second tube section has a pair of radially opposite wings which radially and outwardly extend from the second proximal end at respective positions circumferentially offset from the separation lines.

4. A laryngeal mask airway as recited in claim 3 wherein the first tube section is shorter in length than the second tube section.

5. A laryngeal mask airway as recited in claim 4 further comprising a connector for removably connecting the first proximal end to the second distal end.

6. A laryngeal mask airway as recited in claim 5 wherein the connector has tapered ends and an intermediate portion of substantially uniform diameter along the length thereof.

7. A laryngeal mask airway as recited in claim 6 wherein the second tube section is comprised of polyvinyl chloride, silicone rubber, polyethylene, or tetrafluroethylene.

8. A laryngeal mask airway as recited in claim 7 wherein the first tube section is comprised of silicone rubber.

9. A method of intubating a patient with an endotracheal tube by providing a laryngeal mask airway, and an endotracheal tube having a proximal end, a distal end, and an inflatable cuff adjacent to the distal end, and laryngeal mask airway having an inflatable mask for sealing around the laryngeal inlet of the patient, and also having an airway tube connected to the mask and being adapted to deliver air therethrough to the mask and the patient's laryngeal inlet, the method comprising:

(a) providing an airway tube for the laryngeal mask airway which comprises (i) a first tube section having a first proximal end and a first distal end, the first distal end being connected to the mask, and (ii) a second tube section having a second proximal end and a second distal end, the second distal end being removably connected to the first proximal end, and wherein the second tube section has a pair of radially opposite separation lines longitudinally extending from the second proximal end to the second distal end;

(b) inserting the laryngeal mask airway into the patient so that the mask is positioned immediately adjacent to the patient's laryngeal inlet;

(c) after step (b), inserting the endotracheal tube through the airway tube and through the mask so as to extend into the trachea of the patient;

(d) after step (c), peeling away the second tube section by splitting it apart along the separation lines; and (e) during or after step (d), further inserting the endotracheal tube into the patient's trachea to position the cuff below the vocal cords of the patient.

10. A method as recited in claim 9, further comprising the following step performed after step (d): sliding the mask and first tube section over the endotracheal tube to remove the mask and first tube section from the patient and the endotracheal tube.

11. A method as recited in claim 10 wherein there is further provided a bronchoscope having a fiberoptic tube, and wherein the method further comprises the following step performed after step (b) but before step (c): inserting the fiberoptic tube through the airway tube and through the mask so as to extend into the patient's trachea, such that in step (c) the endotracheal tube is inserted into the patient's trachea by sliding it over the fiberoptic tube.

* * * * *